United States Patent [19]
Quinn

[11] Patent Number: 5,589,629
[45] Date of Patent: Dec. 31, 1996

[54] METHOD AND APPARATUS FOR TESTING VEHICLE EXHAUST EMISSIONS

[76] Inventor: Stephen J. Quinn, 91 Breckonwood Cr., Thornhill, Ontario, Canada, L3T 5G8

[21] Appl. No.: 429,237

[22] Filed: Apr. 25, 1995

[51] Int. Cl.⁶ .................................................. G01N 21/00
[52] U.S. Cl. .......................................... 73/23.31; 73/117.1
[58] Field of Search ...................... 73/117, 23.31, 73/117.1, 865.6

[56] References Cited

U.S. PATENT DOCUMENTS

| | | | |
|---|---|---|---|
| 3,277,703 | 10/1966 | Cline | 73/117 |
| 3,406,562 | 10/1968 | Perna et al. | 73/23.31 |
| 3,427,874 | 2/1969 | Munroe et al. | 73/23.31 |
| 3,581,555 | 6/1971 | Cline | 73/117 |
| 3,603,155 | 9/1971 | Morrio et al. | 73/23.31 |
| 3,630,072 | 12/1971 | Traven | 73/23.31 |
| 3,917,454 | 11/1975 | Clark | 73/23.31 |
| 4,036,592 | 7/1977 | Brown et al. | 73/23.31 |
| 4,126,200 | 11/1978 | Miller et al. | 180/66 R |
| 4,160,373 | 7/1979 | Fastaia et al. | 73/23.31 |
| 4,216,710 | 8/1980 | Asmus | 73/117 |
| 4,466,294 | 8/1984 | Bennington et al. | 73/862.13 |
| 4,494,509 | 1/1985 | Long | 123/416 |
| 4,750,355 | 6/1988 | Urabe et al. | 73/865.6 |
| 4,847,790 | 7/1989 | Suzuki et al. | 73/865.6 |
| 4,924,095 | 5/1990 | Swanson . | |
| 4,964,298 | 10/1990 | Matsushita | 73/117.1 |
| 5,147,426 | 9/1992 | Koike et al. | 73/23.31 |
| 5,210,702 | 5/1993 | Bishop . | |
| 5,241,367 | 8/1993 | Grob . | |
| 5,319,199 | 6/1994 | Stedman . | |
| 5,343,043 | 8/1994 | Johnson . | |
| 5,371,367 | 12/1994 | DiDomenico . | |
| 5,374,992 | 12/1994 | Pye . | |
| 5,401,967 | 3/1995 | Stedman . | |
| 5,418,366 | 5/1995 | Rubin . | |

OTHER PUBLICATIONS

Santa Barbara Research Center, "Remote Emissions Sensor RES–100, SMOG DOG, An Introduction", 1993, entire document.
Santa Barbara Research Center, "Mobile Remote Sensing Device for Vehicle Emissions, Technical Proposal", Oct., 1993, entire document.
ProtectAir Inc., "Description of Live Eye", entire document.

*Primary Examiner*—Richard Chilcot
*Assistant Examiner*—George M. Dombroske
*Attorney, Agent, or Firm*—Riches, McKenzie & Herbert

[57] ABSTRACT

This invention provides a method and apparatus for testing exhaust emissions of vehicles having internal combustion engines. The apparatus of the present invention comprises a test track over which a vehicle is moved under its own power and remote exhaust testers which spectroscopically test exhaust emissions of vehicles as they move over the test track. The apparatus and method of the present invention preferably may be used for pre-screening vehicles as a first step in a testing process utilizing, as a second step, more extensive testing as with stationary testing apparatus. Those vehicles clearly meeting minimum emissions standards can be relatively quickly screened out by the method and apparatus of the present invention and exempted from further, more extensive testing.

19 Claims, 4 Drawing Sheets

METHOD AND APPARATUS FOR TESTING VEHICLE EXHAUST EMISSIONS

FIELD OF THE INVENTION

This invention relates to testing exhaust emissions of vehicles having internal combustion engines.

BACKGROUND OF THE INVENTION

Due to mounting concerns over air quality, numerous jurisdictions in North America, Europe and Asia have instituted mandatory testing programs wherein exhaust emissions of vehicles are tested to determine whether they meet minimum standards set by a government agency. Typically, this testing of exhaust emissions is conducted annually and is a necessary precondition to renewal of vehicle registration. United States government standards for volatile organic compounds, oxides of nitrogen and carbon monoxide as defined by the U.S. Environmental Protection Agency are contained in the Federal Register, Part 51.

It has been found that most vehicles meet emissions standards. Most vehicle-related air pollution is caused by a relatively small proportion of vehicles, many of which have emission control systems which are malfunctioning or have been tampered with.

Presently used tests to accurately determine emission levels and to diagnose problems with vehicle emission controls are time consuming. Typically, vehicles must be brought to a central testing facility, and tested on a stationary testing apparatus by direct sampling of the exhaust.

The disadvantage exists that widespread testing of vehicles using stationary testing apparatus is very time consuming. This results in undue hardship for motorists, who must endure long lineups at testing facilities.

Another disadvantage exists that stationary testing apparatus is very expensive, and therefore the cost of testing a vehicle on stationary apparatus is relatively high.

There are also presently available remote sensing testing apparatus which quickly test exhaust emissions by spectroscopic methods, which may generally be defined as methods which detect the presence of a substance by measurement of the radiant energy absorbed or emitted by the substance in any of the wavelengths of the electromagnetic spectrum. For example, presently available remote sensing testing apparatus typically test exhaust emissions by the use of ultrasensitive infrared detection technology. Remote sensing testing apparatus utilizing ultrasensitive infrared detection technology typically operates by passing a chopped infrared beam through the exhaust plume of a vehicle in close proximity to the exhaust pipe of the vehicle. The absorption intensity of the beam is measured after it is passed through the exhaust plume and the levels of certain target compounds present in the exhaust emissions of the vehicle are then calculated.

In conclusion, the disadvantage exists that accurate testing of vehicle emissions using stationary testing apparatus is time consuming and expensive. Although quicker and cheaper, remote sensing testing is typically less accurate than stationary testing in estimating levels of vehicle emissions.

SUMMARY OF THE INVENTION

The present invention at least partially overcomes these disadvantages by providing an apparatus and a method for testing vehicles which is substantially faster and cheaper than stationary testing apparatus, and provides substantially greater precision than roadside remote sensing testing apparatus.

The apparatus of the present invention comprises a test track over which a vehicle is moved under its own power. The apparatus includes remote sensing exhaust testers positioned along the track to test the exhaust emissions of vehicles as they are driven along the track. The exhaust emissions of the vehicles are preferably tested under at least two different modes of operation to provide a reliable indication of exhaust emissions.

The apparatus and method of the present invention preferably may be used for pre-screening vehicles as a first step in a testing process utilizing, as a second step, more extensive testing as with stationary testing apparatus. Those vehicles, typically comprising a significant portion of vehicles being pre-screened, which clearly meet minimum emission standards, can be relatively quickly screened out and exempted from further testing. The vehicles which do not clearly meet minimum emission standards are then subjected to more extensive testing, as for example, by being tested and diagnosed on a stationary testing apparatus.

Therefore, the method and apparatus of the present invention can be used to eliminate the need for stationary testing of a significant portion of vehicles. By quickly and effectively identifying polluting vehicles, the present invention substantially increases the speed of vehicle emission testing without sacrificing accuracy in the measurement of emission levels.

It is one object of the present invention to provide an improved apparatus and method for testing exhaust emissions of internal combustion vehicles.

It is a further object of the present invention to provide a pre-screening system to quickly identify and separate vehicles which clearly meet emission standards from those which do not or may not.

In one aspect, the present invention comprises a method of testing exhaust emissions of vehicles having internal combustion engines to estimate whether the emissions of any vehicle meet predetermined standards, comprising: moving each vehicle under its own power along a test track under controlled conditions of operation, the test track having an upwardly inclined portion, a horizontal portion and a downwardly inclined portion, the method comprising the steps of: moving the vehicle to ascend the upwardly inclined portion at a positive rate of acceleration and within a first range of velocities, and remotely testing the exhaust emissions of the vehicles by spectroscopic means as the vehicle ascends the upwardly inclined portion at a first test point on the upwardly inclined portion; moving the vehicle across the horizontal portion at a substantially constant velocity and within a second range of velocities, and remotely testing the exhaust emissions of the vehicle by spectroscopic means as the vehicle crosses the horizontal portion at a second test point on the horizontal portion; and moving the vehicle to descend the downwardly inclined portion at a negative rate of acceleration and within a third range of velocities, and remotely testing the exhaust emissions of the vehicle by spectroscopic means as the vehicle descends the downwardly inclined portion at a third test point on the downwardly inclined portion; comparing the test results from the first, second and third test points of one vehicle with results for vehicles which meet the predetermined standards, said steps being performed in any order.

In another aspect, the present invention provides an apparatus for testing exhaust emissions of vehicles having internal combustion engines, comprising: a test track over which vehicles are moved under their own power under controlled conditions of operation, the test track having an upwardly inclined portion, a horizontal portion and a downwardly inclined portion; a first remote sensing tester for testing the exhaust emissions of the vehicles by spectroscopic means, the first tester located at a first test point on the upwardly inclined portion; a second remote sensing tester for testing the exhaust emissions of the vehicles by spectroscopic means, the second tester located at a second test point on the second horizontal portion; a third remote tester for testing the exhaust emissions of the vehicles by spectroscopic means, the third tester located at a third test point on the third inclined portion; and a processor for comparing the test results from the first, second and third test points of one vehicle with results for vehicles which meet the predetermined standards.

Preferably, a stream of air is directed at the track by a blower located ahead of a test point, vehicles passing through the air stream before moving past the test point, the air stream clearing from the track exhaust emissions carried along the track by a vehicle as the vehicle passes through the air stream, the exhaust emissions tested at the test point substantially comprising only an exhaust plume emitted by the exhaust pipe of the vehicle between the air stream and the test point.

More preferably, a stream of air is directed at the track ahead of each test point.

Preferably, the remote testers comprise a source of infrared radiation and a detector of infrared radiation, the source emitting a beam of infrared radiation which passes through an exhaust plume of a vehicle and is subsequently detected by the receiver, the exhaust plume located at the test point and in close proximity to the exhaust pipe of a vehicle.

In yet another aspect, the present invention provides a method of testing exhaust emissions of vehicles having internal combustion engines, comprising: a first pre-screening step, comprising testing vehicles according to the method and apparatus of the present invention described above to estimate whether the emissions of any vehicle meet predetermined standards; and a second step comprising testing exhaust emissions to accurately determine whether the emissions of any vehicle meet predetermined standards, the second step not being conducted for vehicles likely to have emissions meeting the predetermined standard, as estimated by the pre-screening step.

BRIEF DESCRIPTION OF THE DRAWINGS

Further aspects and advantages of the present invention will be apparent from the following description, taken together with the accompanying drawings in which.

DETAILED DESCRIPTION OF THE PREFERRED EMBODIMENTS

Figure 1:
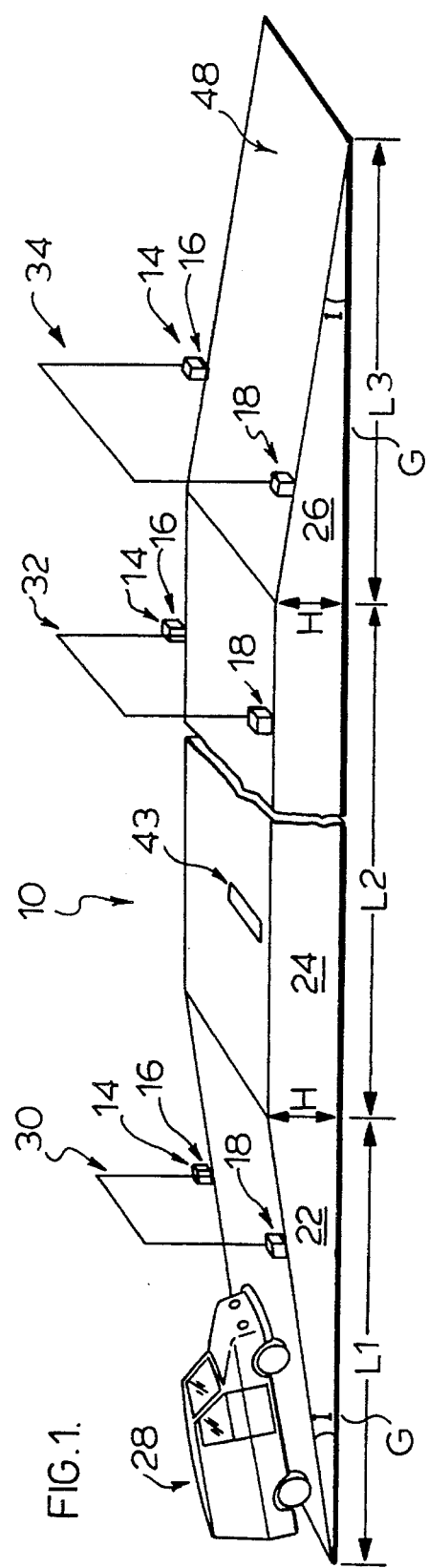
FIG. 1 schematically illustrates a testing apparatus according to a first preferred embodiment of the present invention.

A first preferred testing apparatus according to the present invention is shown in FIG. 1.

The preferred apparatus 10 is shown in FIG. 1 as comprising a test track 12, three remote sensing exhaust testers 14, each comprising a source 16 and a detector 18 located on opposite sides of track 12, and three blowers 20.

FIG. 1 illustrates the test track 12 as comprising three portions; a first, upwardly inclined portion 22, a second, flat, horizontal portion 24, and a third, downwardly inclined portion 26.

Vehicle 28 is moved over track 12 under its own power, first ascending along first inclined portion 22, then moving horizontally along horizontal portion 24, and lastly descending along second inclined portion 26.

Vehicle 28 is moved over track 12 under controlled conditions of acceleration and velocity. Preferably, vehicle 28 starts from a stop at the bottom of first inclined portion 22 and ascends along inclined portion 22 at a constant, positive, rate of acceleration, moves across second horizontal portion 24 with constant velocity, and then descends along the third inclined portion 26 at a constant, negative rate of acceleration.

The exhaust emissions of vehicle 28 are tested at three test points 30, 32 and 34 located along the track 12.

The test points 30, 32 and 34 are illustrated in FIG. 1 as planes through which vehicle 28 passes as it moves along test track 12.

First test point 30 is located proximate the upper end of the first inclined portion 22. At the first test point 30, the vehicle 28 is preferably accelerating at a constant rate up inclined portion 22.

The second test point 32 is located on the second horizontal portion 24, preferably about two thirds of the distance along portion 24. At the second test point 32 the vehicle 28 is preferably moving at constant velocity along central portion 24.

The third test point 34 is located on the third inclined portion 26 proximate its upper end. At the third test point 34, the exhaust emissions of vehicle 28 are tested as it descends along third inclined portion 26, preferably at a constant negative rate of acceleration.

The inventor has determined that the testing of exhaust emissions at the preferred locations of test points 30, 32 and 34 along test track 12 provides a good approximation of exhaust emissions of vehicle 28.

Figure 2:
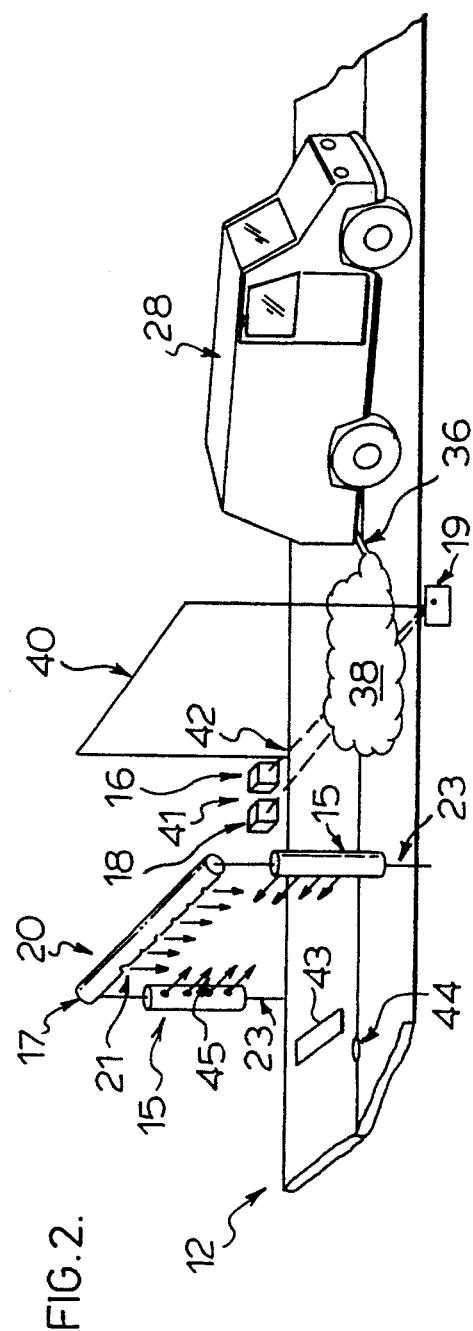
FIG. 2 schematically illustrates a preferred method for testing the exhaust of a vehicle according to the present invention.

FIG. 2 illustrates a preferred manner in which the exhaust emissions of vehicle 28 are tested at one test point along a test track 12.

FIG. 2 illustrates vehicle 28 having a conventional exhaust pipe 36 located at the rear of and underneath vehicle 28. Exhaust pipe 36 forms the terminal end of an exhaust system (not shown) through which exhaust emissions produced by the internal combustion engine powering vehicle 28 are released into the environment.

The exhaust emissions are released from exhaust pipe 36 in the form of an exhaust plume 38, which is a cloud of exhaust matter extending rearwardly from exhaust pipe 36 and located above the surface of test track 12. Typically, the most dense area of exhaust plume 38 is about 8 inches in diameter and is centred about 14 to 16 inches above track 12, depending on the height of exhaust pipe 36.

FIG. 2 illustrates the exhaust plume 38 being tested at test point 40, shown as a plane, by remote sensing exhaust tester 41.

The exhaust plume 38 is preferably tested in close proximity to the end of exhaust pipe 36. Therefore, a sensor is preferably provided along track 12 to sense the passing of vehicle 28 through test point 40 and trigger the exhaust tester 41 to test the exhaust plume 38 of vehicle 28 as the exhaust plume 38 passes through test point 40. The sensor for detecting the passing of vehicle 28 may preferably form an integral part of remote sensing tester 41.

One particularly preferred sensor/trigger mechanism passes a beam across track 12 transverse to the direction of travel of vehicle 12 at test point 40. When the front of vehicle 28 breaks the sensor's beam, the sensor recognizes that the vehicle 28 is passing in front of the sensor. After the rear of vehicle passes through the beam, the beam passes across the track 12 uninterrupted. The sensor then triggers the remote sensing tester to test the exhaust emissions of vehicle 28 proximate exhaust pipe 36. Preferably, there is a short time delay between the instant the vehicle 28 finishes passing through the beam and the triggering of the remote sensing tester to allow plume 38, located rearwardly of vehicle 28, to move to test point 40.

The remote sensing exhaust tester 41 comprises a source of electromagnetic radiation 16 and a detector 18 which detects electromagnetic radiation emitted by source 16.

Electromagnetic radiation may be defined as radiant energy in the form of electromagnetic waves, or light. The various forms of electromagnetic radiation comprising the electromagnetic spectrum are characterized by their wavelengths, and include cosmic rays, gamma rays, x-rays, UV rays, visible light rays, infrared, microwave and radiofrequency rays. Preferably, the electromagnetic radiation emitted by source 16 and received by detector 18 comprises UV or infrared, more preferably infrared of one or more wavelengths. Although UV and infrared are preferred in the method and apparatus of the present invention, it is to be understood that electromagnetic radiation of other wavelengths may also be suitable.

Most preferably, source 16 emits a beam 42 comprising infrared radiation of at least one wavelength, each wavelength interacting with a target compound present in the exhaust emissions of vehicle 28.

The beam 42 of infrared radiation emitted by source 16 is directed transversely across track 12 in the plane of test point 40.

FIG. 2 illustrates a particularly preferred tester 41 wherein the source 16 and detector 18 are located on the same side of track 12. The beam passes from source 16, through exhaust plume 38, to a reflector 19 on the opposite side of track 12. Reflector 19 reflects the beam back to detector 18, through exhaust plume 38.

The path length travelled by the beam is preferably about 25 feet, which is preferably about twice the width of track 12. Therefore, the configuration of tester 41 shown in FIG. 2 is preferably used when it is desired to locate tester 41 directly alongside track 12. However, it is to be understood that locating source 16 and detector 18 on opposite sides of track 12, as shown in FIG. 1, may be equally suitable.

The absorption intensity of the infrared radiation received by detector 18 is compared with the intensity of the infrared radiation emitted by source 16 to provide a measurement representative of the quantity of one or more target compounds in the exhaust plume 38 of vehicle 28.

The beam 42 emitted by source 16 preferably passes through the centre of exhaust plume 38, and in close proximity to the end of exhaust pipe 36. For vehicles such as vehicle 28 shown in FIG. 2 having an exhaust pipe 36 slightly above track 14, the height of beam 42 is preferably about 12 to about 20 inches above the level of track 12, more preferably about 14 to about 16 inches above track 12.

The acceleration and velocity of vehicle 28 are preferably monitored as it passes over track 12 to determine whether the motion of vehicle 28 is within predetermined parameters of velocity and acceleration. One preferred monitoring device is a piezoelectric strip 43 attached to track 12. The strip 43 can be used to determine the velocity of vehicle 28 by measuring the time taken for one tire to move over strip 43. The acceleration can be determined by measuring the relative velocities of one front tire and one rear tire of vehicle 12 over strip 43.

Although FIGS. 1 and 2 show only one piezoelectric strip 43, it is to be understood that any number of strips 43 may be positioned along track 12, and that strips 43 may be positioned at any desired interval, for example every 5 feet. Although not shown in FIG. 5 for convenience, it is to be understood that strips 43 are also preferably positioned along track 50 of FIG. 5.

The reliability of the test results is at least partially dependent on the quality of the exhaust plume 38 emitted by vehicle 28. Environmental factors such as wind and rain tend to disperse the plume 38, causing unreliable test results. Therefore, the test track 12 is preferably sheltered from wind and precipitation, preferably within a building or shelter.

Water may also be brought onto test track 12 by the vehicles being tested. For example, water entrained in tire treads or ice and snow attached to the chassis of a vehicle may be deposited on track 12. This water wets track 12 and may be sprayed upwardly by the wheels of vehicles as they move over track 12 placing water into the path of the emitted beam 42 from the tester 41 and possibly affecting the test results. This problem can be reduced by shaping track 12 so that water deposited on track 12 drains to the centre of track 12 and away from the paths of vehicle wheels. Preferably, as shown in FIG. 2, track 12 has a slightly V-shaped transverse cross-section and is provided with drains 44 at its centre so that water collecting in the centre of track 12 can be drained away.

The inventor has also found that exhaust fumes collect under vehicle 28 and are entrained by vehicle 28 as it moves along track 12. If these entrained exhaust fumes are present when vehicle 28 passes test point 40, less accurate test results will be obtained since the exhaust fumes entrained by vehicle 28 will mix with the exhaust plume 38 being tested at test point 40. The entrained exhaust fumes may contain exhaust emissions emitted under different conditions than at the test point 40 and which may not be generally representative of the exhaust emissions of vehicle 28 at test point 40.

Therefore, as shown in FIG. 2, blowers 20 are preferably positioned proximate track 12 to blow an air curtain 45 onto track 12. The blower 20 preferably blows air substantially vertically downward onto track 12 and also substantially transverse to track 12. Preferably, the air flow is directed slightly rearwardly relative to the direction of travel of a vehicle 28. The blower 20 is preferably positioned so that air curtain 45 can "break" exhaust plume 38 shortly before vehicle 28 passes test point 40. The inventor has found that directing air flow slightly rearwardly more efficiently breaks the plume as vehicle 28 moves past a blower 20.

The distance between air curtain 45 and test point 40 must be carefully controlled so that the exhaust plume 38 has sufficient time to re-establish itself between air curtain 45 and test point 40. The preferred distance between air curtain 45 and test point 40 is dependent on the velocity and acceleration of vehicle 28.

Thus, when vehicle 28 passes through test point 40, substantially the only exhaust present will be that released from exhaust pipe 36 in the form of exhaust plume 38, the exhaust plume 38 forming between air curtain 45 and test point 40.

Preferably, a blower 20 is located along track 12 ahead of each test point on the test track 12. Although not shown in FIG. 1, a blower 20 is preferably located ahead of each test point 30, 32 and 34 in order to break the exhaust plume of vehicle 28, while being located a sufficient distance from the test point to allow the exhaust plume of vehicle 28 to reestablish itself for testing at each test point 30, 32 and 34.

As shown in FIG. 2, blower 20 preferably comprises two vertical pipes 15 and a horizontal pipe 17 each provided with a row of holes 21, the holes 21 being directed downwardly toward track 12 by horizontal pipe 17 and transversely across track 12 by vertical pipes 15. A source of air (not shown) supplies pressurized air to blower 20. As shown in FIG. 2, blower 20 may preferably be supported on legs 23.

It is preferred that vehicle 28 be tested under at least two different modes of operation, defined by one or more of velocity, acceleration, engine speed and the ratio of air to hydrocarbon fuel being consumed. These factors have an impact on the composition of the exhaust emissions.

The vehicle 28 preferably moves up first inclined portion 22 in a "loaded" mode. In loaded mode, the vehicle is preferably accelerating up inclined portion 22, more preferably at a constant rate. To achieve loaded mode, vehicle 28 is preferably stopped at the bottom of first inclined portion 22 before beginning its ascent along inclined portion 22. In the loaded mode, because the accelerator pedal is depressed by the driver, the engine speed is moderately high, preferably about 2,000 rpm, and the air:fuel ratio is moderately enriched, preferably in the range of from about 14.7:1, the stoichiometric ratio for ordinary gasolines, to about 13.5:1. It is to be understood that loaded mode differs from "enriched" mode, wherein the accelerator pedal is substantially fully depressed and the air:fuel ratio is enriched to below about 13.5:1.

The vehicle 28 preferably moves across horizontal portion 24 in "cruise" mode, wherein vehicle 28 is moving with substantially constant velocity. In cruise mode, the accelerator pedal is partially depressed, preferably less than in loaded mode, and therefore the engine speed in cruise mode is less than that in loaded mode, preferably from about 800 rpm to about 1500 rpm. The air:fuel ratio in cruise mode is leaner than that in loaded mode, preferably from about 14.0:1 to about 15.0:1.

On second inclined portion 26, vehicle 28 is in "deceleration" mode, and is preferably decelerated by engine braking along at least a portion of second inclined portion 26. In deceleration mode, the acceleration pedal is not depressed, the engine speed is preferably less than that in cruise mode and the air:fuel ratio is preferably leaner than that in cruise mode.

It is to be understood that the above engine speeds and air:fuel ratios are only rough estimates and that the engine speeds and air:fuel ratios discussed above would not be applicable to all vehicles.

The test track 12 shown in FIG. 1 may have any suitable dimensions. The inclined portions 22 and 26 may have different dimensions and slopes, although they are shown in FIG. 1 as preferably having substantially the same dimensions. Preferably, an angle of incline I measured between reference plane G defined by the base of track 12 and the upper surface 46 of first inclined portion 22 and between reference plane G and the upper surface 48 of second inclined portion 26 is from about 2° to about 10°. Most preferably, the angle of incline I of the inclined portions 22 and 26 is about 6°.

The lengths of inclined portions 22 and 26, as measured along reference plane G, are respectively designated L1 and L3 in FIG. 1.

Preferably, the length L1 of inclined portion 22 is long enough to attain loaded mode and the length L3 of the inclined portion 26 is long enough to attain deceleration mode. More preferably, L1 and L3 are from about 30 to about 100 feet. Most preferably, the lengths L1 and L3 are about 63 feet.

The inclined portions 22 and 26 preferably have the same height H, which is defined as the maximum vertical rise of the inclined portions 22 and 26 above reference plane G. Preferably, height H is from about 2 to about 8 feet. Most preferably, height H is about 4 feet.

The length L2 of the horizontal portion 24 is long enough for vehicle 28 to change from loaded mode to cruise mode. Length L2 is preferably from about 40 to about 200 feet, more preferably about 89 feet.

The preferred test track 12 illustrated by FIG. 1 is elevated above reference plane G. However, it is to be appreciated that test track 12 may have numerous configurations. Firstly, test track 12 may comprise one or more inclined portions, with the preferred number of inclined portions being two, as shown in FIG. 1, and the test track may comprise more than one flat, horizontal portion. Secondly, the test track 12 is not necessarily raised above ground level, but may also be partially or wholly situated at or below ground level.

Figure 3:
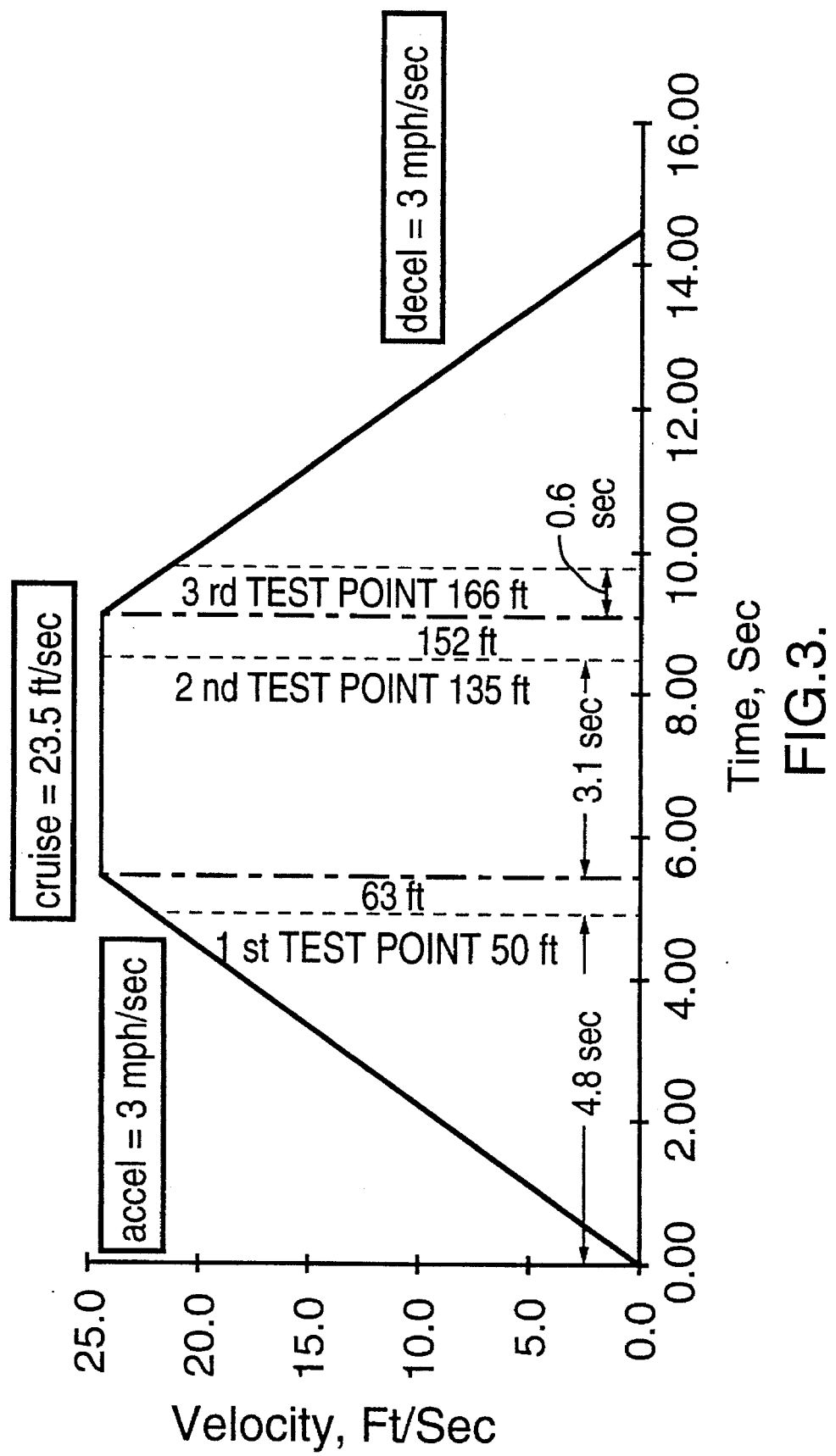
FIG. 3 is a plot of velocity in feet per second versus distance in feet showing preferred conditions for velocity and acceleration in a preferred testing method of the present invention utilizing the apparatus shown in FIG. 1.
Figure 4:
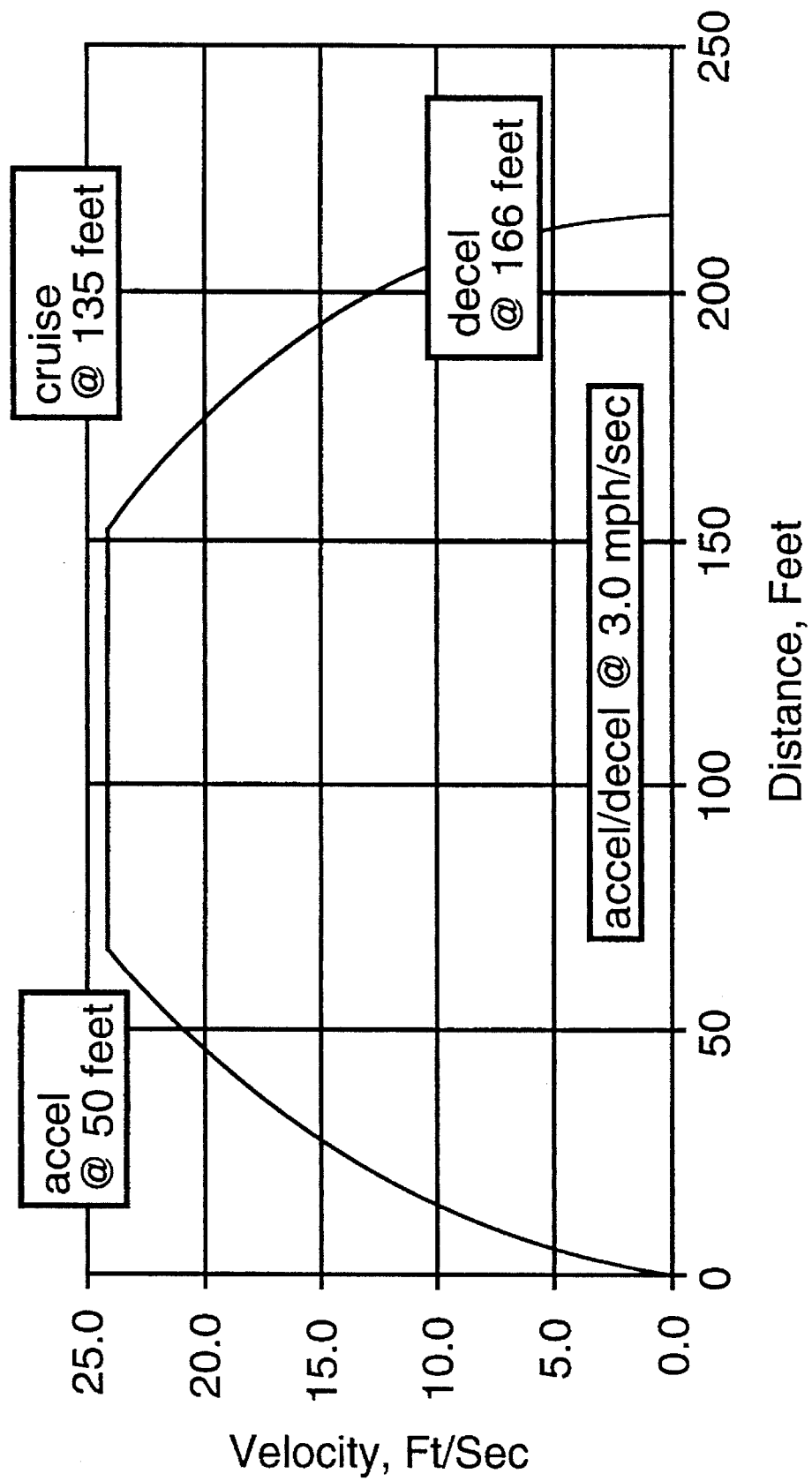
FIG. 4 is a plot of velocity in feet per second versus time in seconds for the velocity and acceleration conditions shown in FIG. 2.

With reference to the preferred apparatus shown in FIG. 1, FIGS. 3 and 4 are plots of velocity versus time and velocity versus distance, respectively, illustrating preferred conditions of velocity and acceleration under which vehicle 28 is driven over a particularly preferred test track 12, having angle I of 6°, H of 4 feet, L1 and L3 both 63 feet and L2 of 89 feet.

FIGS. 3 and 4 show that the velocity of vehicle 28 in loaded mode preferably increases at a constant rate of 3 mph/sec (4.4 ft/sec$^2$) as it is driven over upwardly inclined portion 22. At the upper end of inclined portion 22, vehicle 28 reaches a maximum velocity of 23.5 ft/sec, this velocity being reasonably constant as vehicle 28 passes over horizontal portion 24 in cruise mode. When the vehicle 28 reaches downwardly inclined portion 26, it is preferably decelerated at a constant rate of 3 mph/sec.

The inventor has found that the first test point 30 is most preferably located at a distance of about 50 feet from the lower end of inclined portion 22, the second test point 32 is most preferably located about 72 feet from the beginning of horizontal portion 24, and third test point 34 is preferably located about 14 feet from the upper end of inclined portion 26. Regarding third test point 34, the inventor has found that the vehicle 28 is preferably tested after the vehicle has attained deceleration mode and after engine braking has begun.

Remote sensing exhaust testers 14 and 41 such as those described above in reference to FIGS. 1 and 2 are commercially available. One particularly preferred remote sensing exhaust tester is the RES-100 unit of the Santa Barbara Research Center, a subsidiary of Hughes Aircraft Company, sold under the trade mark "SMOG DOG". Remote sensing exhaust testers typically operate by measuring selective absorption of infrared radiation by one or more of carbon monoxide, carbon dioxide, hydrocarbons, nitrogen oxides NO$_x$, wherein X is ½ to 3, and oxygen, some or all of which may be present in exhaust of vehicles having internal combustion engines.

The apparatus of the present invention is preferably initially calibrated so that it provides test results reasonably consistent with test results provided by means which are known to be accurate, such as stationary testing apparatus.

The calibration process preferably comprises testing exhaust emissions of vehicles using the method of the invention, and comparing the test results obtained according to the present invention with test results obtained by other methods known to be accurate. A correlation is determined between the test results obtained according to the present invention and the exhaust emissions accurately determined by other methods.

Using the correlation, it can be determined, with varying levels of probability, whether any vehicle tested according to the present invention will meet predetermined standard levels of emissions, for example as prescribed by a government agency.

To improve the correlation between the test results according to the present invention and the levels of exhaust emissions accurately determined by other methods, the rate of acceleration and the velocity of each vehicle are preferably carefully controlled as the vehicle passes each test point along the test track.

Therefore, it is most preferred that the vehicles be driven over the track by experienced test drivers capable of keeping velocity and acceleration within preset parameters. However, it is to be appreciated that the apparatus of the present invention can be calibrated to allow vehicle owners to drive their own vehicles over the test track. However, the test results would likely be more accurate when the vehicles are driven by skilled drivers.

When used as a pre-screening step, the method of the present invention is preferably used to identify vehicles whose emissions with a very high level of certainty, meet standards more strict than the predetermined standard.

For pre-screening, it is not necessary that the method of the present invention identify a high percentage of vehicles whose emissions meet the predetermined standard, only that at least some of these vehicles are identified and exempted from further, more extensive, testing. Reducing the number of vehicles subjected to extensive testing would attain at least one of the objects of the present invention.

If the most preferred dimensions of the track 12 shown in FIG. 1 are used, with L1 and L3 equal to 63 feet and L2 equal to 89 feet, the total length of test track 12 will be 215 feet. Although the test track 12 is of a simple design, it would require a relatively large amount of space.

Figure 5:
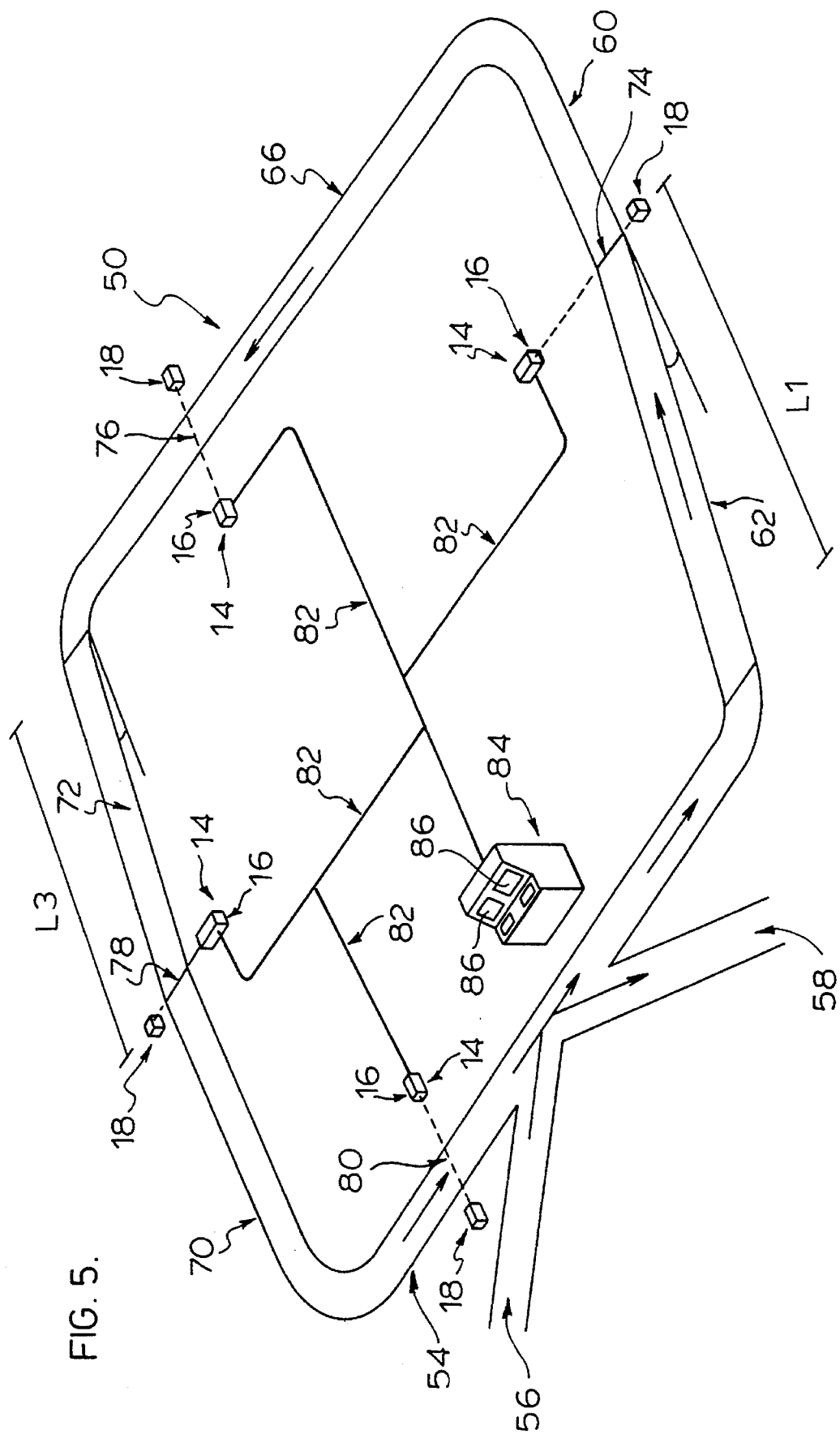
FIG. 5 illustrates a testing apparatus according to a second preferred embodiment of the present invention.

FIG. 5 illustrates a second preferred test track 50 according to the present invention. Test track 50 is a four cornered loop having four straight sides, all sides having the same length. The preferred length of the sides is from about 20 to about 60 feet, with about 40 to about 50 feet being most preferred. This track is preferable over that shown in FIG. 1 when space is limited.

The first side 54 of track 50 is provided with an entrance ramp 56 and an exit ramp 58 by which vehicles (not shown) may enter and leave the test track 50, respectively.

Second side 60 of track 50 has a downward inclined portion 62 of length L1. Downward incline 62 is preferably at an angle of about 5° to about 10° to the horizontal, most preferably 6°, with length L1 preferably being about 30 feet.

The third side 66 of test track 50 is flat and horizontal.

The fourth side 70 of test track 50 preferably has an upwardly inclined portion 72 of length L3. Preferably, the angle of incline 72 is from about 5° to about 10° from the horizontal, most preferably 6°. Preferably, length L3 is about 20 to 30 feet.

Preferably, a vehicle 28 (not shown) enters the first side 54 of test track 50 via entrance ramp 56 and moves along test track 50 in the direction of the arrows in FIG. 5. Vehicle 28 is moved in deceleration mode, preferably at a constant negative rate of acceleration, over the downwardly inclined portion 62, with the exhaust emissions of vehicle 28 being tested at first test point 74 located at the lower end of inclined portion 62.

The vehicle 28 preferably moves along the entire length of third side 66 in a cruise mode, preferably at a constant velocity. The exhaust emissions of vehicle 28 are tested as it moves past the second test point 76 located on the third side 66 of test track 50.

On the fourth side 70 of test track 50, the vehicle is preferably accelerated in loaded mode at a constant rate of acceleration along upwardly inclined portion 72. The exhaust emissions of vehicle 28 are again tested at the third test point 78 located at the upper end of inclined portion 72.

The vehicle 28 then proceeds along test track 50 back to the first side 54. The vehicle exhaust may preferably be tested at fourth test point 80 along first side 54, vehicle 28 moving in cruise mode, preferably at a constant velocity, past test point 80. The vehicle can then either leave test track 50 by exit ramp 58, which adjoins first side 54, or may make another circuit of test track 50.

At each of the test points 74, 76, 78 and 80 along test track 50 are located remote exhaust testers 14 comprising a source 16 and detector 18. These testers 14 are shown as being identical to those described above in reference to FIG. 1, however the source 16 and detector 18 may be on the same side of track 50 as shown in FIG. 2.

Although not shown in FIG. 5, a blower 20 such as that shown in FIG. 2 is preferably positioned ahead of each test point 74, 76, 78 and 80 to break the exhaust plume with a curtain of air 45, a blower 20 being located a sufficient distance ahead of each test point to allow the exhaust plume to reestablish itself at the test point.

As shown by FIG. 5, the three remote exhaust testers 16a, 16b and 16c are each connected by wires 82 to a main console 84.

Console 84 is preferably provided with a processor (not shown) which processes the test results, correlates the results of individual tests, and compares the exhaust emissions determined by the tests with a predetermined standard.

Each test result is preferably processed to determine firstly, whether or not instantaneous values of velocity and acceleration of a vehicle moving past a test point fall within predetermined ranges of velocity and acceleration; and secondly, whether or not average values of velocity and acceleration for movement of a vehicle over the entire test track, or any portion thereof, fall within predetermined ranges of velocity and acceleration.

If the velocity and/or acceleration are not within the predetermined ranges, then one or more test results may preferably be discarded. On the other hand, if the velocity and/or acceleration are within predetermined ranges, then the processor preferably calculates the vehicle's exhaust emissions based on the instantaneous and average velocity and acceleration of the vehicle.

Velocity and acceleration may preferably be measured by piezoelectric strips, such as strips 43 shown in FIG. 2, located at specified points along the test track, to determine the velocity and acceleration of the vehicle. Velocity may preferably be measured by determining the time required for one tire of the vehicle to pass over a strip 43, and acceleration may preferably be determined by measuring differences in velocity between a front and a rear tire of the vehicle.

The processor preferably generates a profile of the velocity and acceleration of the vehicle as it moves over the test track. This profile shows whether or not movement of the vehicle is maintained within predetermined ranges for average velocity and acceleration over any portion of the test track, and whether or not the instantaneous velocity and acceleration of the vehicle at any test point is within predetermined ranges of instantaneous velocity and acceleration.

The results of individual tests may individually be compared against the predetermined standard. Preferably, for the vehicle to pass the emissions test, at least two of the test results must meet the predetermined standard.

Although the test results can be individually compared to the predetermined standard, it is more preferred that the test results be correlated to determine a composite level of emissions standards for the vehicle, this composite being compared against the predetermined standard. Preferably, a formula is utilized by the processor which combines test results obtained under different conditions of velocity and acceleration to obtain the composite emissions level for the vehicle.

In one preferred embodiment, the composite emissions level is the average of the emissions levels determined at each test point.

Although certain preferred methods for correlating test results and comparing them to a predetermined standard have been described above, it is to be appreciated that specific methods of correlating and comparing test results may be prescribed by government agencies in certain jurisdictions in which testing is carried out. Therefore, the processor may preferably be programmable so that it may be adapted for use in different jurisdictions requiring different methods of correlating and comparing test results.

Although FIGS. 1 and 5 illustrate the test points being located at specific locations along test tracks 12 and 50, it is to be understood that the positioning of the test points is variable.

Although test tracks 12 and 50 are shown as having inclined portions, it is to be appreciated that a test track according to the present invention could be designed which is substantially flat and horizontal throughout its entire length. Vehicles would be driven along such a track and tested at two or more test points under predetermined conditions of velocity and acceleration. The velocity and acceleration of the vehicle would be substantially entirely controlled by the vehicle driver.

Although the invention has been described in connection with certain preferred embodiments, it is not intended that it be limited thereto. Rather, it is intended that the invention cover all alternate embodiments as may be within the scope of the following claims.

I claim:

1. A method of spectroscopic testing of exhaust emissions of vehicles having internal combustion engines to estimate whether the emissions of any vehicle meet predetermined standards, comprising:

moving each said vehicle under its own power along a test track under controlled conditions of operation, said test track having an upwardly inclined portion, a horizontal portion and a downwardly inclined portion, the method comprising the steps of:

(a) moving the vehicle to ascend the upwardly inclined portion at a positive rate of acceleration and within a predetermined first range of velocities, and remotely testing the exhaust emissions of the vehicle by spectroscopic means as the vehicle ascends the upwardly inclined portion at a first test point on the upwardly inclined portion;

(b) moving the vehicle across the horizontal portion at a substantially constant velocity and within a predetermined second range of velocities, and remotely testing the exhaust emissions of the vehicle by spectroscopic means as the vehicle crosses the horizontal portion at a second test point on the horizontal portion; and (c) moving the vehicle to descend the downwardly inclined portion at a negative rate of acceleration and within a predetermined third range of velocities, and remotely testing the exhaust emissions of the vehicle by spectroscopic means as the vehicle descends the downwardly inclined portion at a third test point on the downwardly inclined portion;

comparing the test results from the first, second and third test points of one vehicle with results for vehicles which meet the predetermined standards, said steps (a), (b) and (c) being performed in any order.

2. The method of claim 1, wherein step (a) is performed first, step (b) is performed second, and step (c) is performed third.

3. The method of claim 1, wherein:

in step (a) the vehicle is operated in a loaded mode with an air:fuel ratio in the range of about 13.5:1 to about 14.7:1;

in step (b), the vehicle is operated in a cruise mode with an air:fuel ratio in the range of about 14.0:1 to about 15.0:1; and in step (c), the vehicle is operated in a deceleration mode with an air:fuel ratio greater than the air:fuel ratio in the cruise mode.

4. The method of claim 3, wherein:

in step (a) the vehicle is moved along the upwardly inclined portion at a constant, positive rate of acceleration; and in step (c) the vehicle is moved along the downwardly inclined portion at a constant, negative rate of acceleration.

5. The method of claim 1, wherein:

in step (a) the vehicle is moved along the upwardly inclined portion at a constant, positive rate of acceleration; and in step (c) the vehicle is moved along the downwardly inclined portion at a constant, negative rate of acceleration.

6. The method of claim 1, wherein said inclined portions are inclined at an angle of about 2° to about 10° relative to a horizontal reference plane and have a length of about 30 feet to about 100 feet, measured along the reference plane, and said horizontal portion has a length of about 40 to about 200 feet.

7. The method of claim 1, wherein a stream of air is directed at the track ahead of a test point, vehicles passing through said air stream before moving past said test point, said air stream clearing from the track exhaust emissions carried along the track by a vehicle as said vehicle passes through said air stream, the exhaust emissions tested at the test point substantially comprising only an exhaust plume emitted by exhaust pipe means of said vehicle between the air stream and the test point.

8. The method of claim 7, wherein a stream of air is directed at the track ahead of each test point.

9. The method of claim 1, wherein said remote testing is performed by remote sensing testing means located at each test point, comprising:

a source of infrared radiation;

and a detector of infrared radiation;

said source emitting a beam of infrared radiation which passes through an exhaust plume of a vehicle, and is subsequently received by the detector, said exhaust plume located at the testing point and in close proximity to exhaust pipe means of a vehicle.

10. The method of claim 1, wherein the velocity and acceleration of each said vehicle are measured at said test points and at predetermined locations along said test track to determine whether or not the velocity and acceleration of each said vehicle fall within predetermined ranges of velocity and acceleration.

11. A method of testing exhaust emissions of vehicles having internal combustion engines, comprising:

(a) a first pre-screening step, comprising testing vehicles according to the method of claim 1, to estimate whether the emissions of any vehicle meet predetermined standards; and (b) a second step comprising testing exhaust emissions to accurately determine whether the emissions of any vehicle meet predetermined standards, said second step not being conducted for vehicles likely to have emissions meeting the predetermined standard, as estimated by the pre-screening step.

12. The method of claim 11, wherein said inclined portions are inclined at an angle of about 2° to about 10° relative to a horizontal reference plane and have a length of about 30 feet to about 100 feet, measured along the reference plane, and said horizontal portion has a length of about 40 to about 200 feet.

13. The method of claim 11, wherein said remote testing is performed by remote sensing testing means located at each test point, comprising:

a source of infrared radiation;

and a detector of infrared radiation;

said source emitting a beam of infrared radiation which passes through an exhaust plume of a vehicle, and is subsequently received by the detector, said exhaust plume located at the testing point and in close proximity to exhaust pipe means of a vehicle.

14. The method of claim 11, wherein the velocity and acceleration of each said vehicle are measured at said test points and at predetermined locations along said test track to determine whether or not the velocity and acceleration of each said vehicle fall within predetermined ranges of velocity and acceleration.

15. An apparatus for spectroscopic testing of exhaust emissions of vehicles having internal combustion engines, comprising:

(a) a test track over which vehicles are moved under their own power under controlled conditions of operation, said test track having an upwardly inclined portion, a horizontal portion and a downwardly inclined portion;

(b) first remote sensing testing means for testing the exhaust emissions of the vehicles by spectroscopic means, said first testing means located at a first test point on the upwardly inclined portion, so as to test the vehicles in a first mode of operation;

(c) second remote sensing testing means for testing the exhaust emissions of the vehicles by spectroscopic means, said second testing means located at a second test point on the horizontal portion, so as to test the vehicles in a second mode of operation;

(d) third remote sensing testing means for testing the exhaust emissions of the vehicles by spectroscopic means, said third testing means located at a third test point on the downwardly inclined portion, so as to test the vehicles in third mode of operation; and (e) processing means for comparing the test results from the first, second and third test points of one vehicle with results for vehicles which meet the predetermined standards.

16. The apparatus of claim 15, further comprising:

(f) blower means located ahead of a test point, said blower means blowing a stream of air directed at the track ahead of a test point, vehicles passing through said air stream before moving past said test point, said air stream clearing from the track exhaust emissions carried along the track by a vehicle as said vehicle passes through said air stream, the exhaust emissions tested at the test point substantially comprising only an exhaust plume emitted by exhaust pipe means of said vehicle between the air stream and the test point.

17. The apparatus of claim 16, wherein blower means are located ahead of each test point.

18. The apparatus of claim 15, wherein said inclined portions are inclined at an angle of about 2° to about 10° relative to a horizontal reference plane and have a length of about 30 feet to about 100 feet, measured along the reference plane, and said horizontal portion has a length of about 40 to about 200 feet.

19. The apparatus of claim 15, wherein said remote sensing testing means located at each test point comprises:

a source of infrared radiation and a detector of infrared radiation, said source emitting a beam of infrared radiation which passes through an exhaust plume of a vehicle and is subsequently received by the detector, said exhaust plume located at the test point and in close proximity to exhaust pipe means of a vehicle.

* * * * *